United States Patent [19]
Kiesow

[11] Patent Number: 5,581,015
[45] Date of Patent: Dec. 3, 1996

[54] DEVICES AND METHODS FOR MEASURING TEMPERATURE AND VAPOR LEVELS IN A GAS

[76] Inventor: Lutz A. Kiesow, 128 Del Prado St., Lake Oswego, Oreg. 97035

[21] Appl. No.: 384,964
[22] Filed: Feb. 7, 1995
[51] Int. Cl.$^6$ .............................. G01N 19/10; G01K 1/16
[52] U.S. Cl. .................... 73/29.01; 73/29.02; 73/335.08; 73/335.06; 374/121
[58] Field of Search .............................. 73/29.01, 29.02, 73/335.01, 335.06, 335.08, 335.09; 374/120, 121

[56] References Cited

U.S. PATENT DOCUMENTS

| | | |
|---|---|---|
| 2,621,297 | 12/1952 | Obermaier . |
| 3,041,878 | 7/1962 | McInroy .................................. 73/29.02 |
| 3,196,683 | 7/1965 | Gross .................................... 73/335.08 |
| 3,412,599 | 11/1968 | Hammons et al. . |
| 3,636,768 | 1/1972 | Tinet et al. . |
| 3,817,102 | 6/1974 | Shea ..................................... 73/335.06 |
| 4,103,224 | 7/1978 | Taro et al. . |
| 4,461,167 | 7/1984 | Kent et al. . |
| 4,526,034 | 7/1985 | Campbell et al. . |
| 4,627,284 | 12/1986 | Gersh et al. . |
| 4,809,537 | 3/1989 | Glover et al. ......................... 73/335.08 |
| 4,872,340 | 10/1989 | de Yong . |
| 5,016,472 | 5/1991 | Amrhein et al. ....................... 73/29.02 |
| 5,148,710 | 9/1992 | Gudehus et al. . |
| 5,227,636 | 7/1993 | Schwiesow . |

FOREIGN PATENT DOCUMENTS

| | | | |
|---|---|---|---|
| 3737260 | 3/1989 | Germany | .............................. 73/29.01 |
| 296152 | 11/1989 | Japan | .................................. 73/29.02 |
| 298412 | 12/1989 | Japan . | |

OTHER PUBLICATIONS

F. Pompei et al., *Infrared Thermocouples–Temperature without Touching*.
Nantou, "Digital Ventilated Psychrometer", IEEE Transactions on Instrumentation and Measurement, vol. IM–28, No. 1, Mar. 1979, pp. 42–45.
Webster's Third New International Dictionary of the English Language Unabridged, 1964, p. 1579.
Webster's II New Riverside University Dictionary, 1988, p. 822.

Primary Examiner—Hezron E. Williams
Assistant Examiner—Daniel S. Larkin
Attorney, Agent, or Firm—Kolisch, Hartwell, Dickinson, McCormack & Heuser

[57] ABSTRACT

Devices relating to a psychrometer employing an infrared thermocouple aimed at a wet surface, and another infrared thermocouple aimed at a dry surface, are described. The wet surface is continuously supplied with liquid, for example, $H_2O$. The infrared thermocouple which is aimed at the wet surface detects evaporative heat loss instantaneously at the wet surface as it occurs, without coming into contact with the wet surface.

13 Claims, 2 Drawing Sheets

DEVICES AND METHODS FOR MEASURING TEMPERATURE AND VAPOR LEVELS IN A GAS

FIELD OF THE INVENTION

The invention involves measurement of vapor levels, for example, humidity, and temperature of a gas. In particular, the invention relates to a device which employs infrared thermocouples to measure changes in vapor concentration and temperature of a gas.

BACKGROUND OF THE INVENTION

It is often necessary to monitor the relative humidity of a gas. For example, product manufacturing processes often include one or more steps which must be carried out within a tightly controlled humidity range. Also, in order to maximize the shelf life of some products, it is necessary to minimize humidity in the atmosphere where the product is packaged. Another example where it is important to monitor relative humidity levels is in greenhouses. Additionally, it is important to monitor relative humidity levels in an incubator which contains a subject, such as a prematurely born infant, where temperature, humidity and oxygen levels must be carefully controlled. In such a system, it is often desirable to monitor the subject's rate of metabolism which is relatable to the subject's evaporative heat loss, which in turn affects the humidity level of the gas in the incubator.

Numerous devices have been used in the past to monitor the humidity of a gas. One class of humidity measuring devices includes psychrometers. U.S. Pat. No. 4,461,167 describes numerous examples of psychrometer devices. Psychrometers generally employ two thermocouples, one of which monitors the dry-bulb temperature of a gas flow, and the second of which is embedded in a moistened wick along the same gas flow. Changes in humidity should not affect the dry-bulb temperature of the first thermocouple. However, the temperature reading of the second thermocouple is affected by changes in humidity of the gas because, depending on the relative humidity of the gas, more or less liquid evaporates from the wick. Therefore, the difference between temperature readings of the first and second thermocouples indicates relative changes in humidity of the gas.

There are several significant disadvantages which present themselves with psychrometers of the prior art. First, the "second" thermocouple's sensing of evaporative heat loss from the moistened wick is relatively indirect because evaporation primarily occurs at the wick's surface, whereas the thermocouple's sensor resides in a sub-surface, internal portion of the wick. Temperature changes inside the wick which are due to evaporative heat loss are diminished in magnitude and delayed in comparison to temperature changes which occur at the wick's surface. Another disadvantage with psychrometers in the prior art is that their response to a change in humidity of a gas is relatively slow, i.e., the time it takes for a temperature change at the wick's surface to cause a temperature change inside the wick. The heat transfer process may take up to several minutes depending on how deeply into the wick the thermocouple sensor penetrates. A psychrometer which takes minutes to detect humidity changes cannot be used effectively in situations where humidity levels are changing rapidly, i.e., fractions of minutes or seconds.

Another type of device which has been used to measure atmospheric humidity is referred to as a hygrometer. In a hygrometer, for example, the one disclosed in U.S. Pat. No. 3,636,768, identical infrared beams pass through two enclosures, one of which contains dry air, and the other of which contains sample air whose humidity is to be measured. An infrared detector receives the two beams. The difference between the levels of detectable infrared light from the two beams indicates the relative humidity level of the sample gas because water molecules in the sample gas absorb infrared light. A hygrometer is relatively more complex than a psychrometer because it requires a light source and a dry gas source. The relative dryness of the dry gas source must be tightly controlled and monitored, otherwise the humidity determination of the sample gas may be invalid or unreliable.

Accordingly, one object of the present invention is to provide a device capable of measuring relative humidity in a gas, rapidly, and preferably instantaneously.

Another object of the invention is for the device to measure relative humidity without requiring a source of dry gas for comparison.

SUMMARY OF THE INVENTION

The above objects and other important objectives are achieved by the present invention which provides, among other things, a device for measuring a relative humidity level of a gas. The device of the invention includes an absorbent body, such as a wick. An infrared emanation sensor, preferably a thermocouple, is directed toward a surface of the body and is capable of measuring changes in infrared emanation at the surface while a gas is passed across that surface.

In a preferred embodiment of the invention, the device is a psychrometer including first and second chambers. The first chamber contains a liquid. The second chamber has a gas inlet and a gas outlet. A wick is partially immersed in liquid contained in the first chamber and extends into the second chamber where the wick presents a surface which receives a constant supply of liquid by capillary action from the first chamber. A first infrared thermocouple is directed toward, without contacting, the surface of the wick. A second infrared thermocouple is directed toward a standard, non-absorbent surface present within the second chamber.

Also encompassed by the present invention, is a method of measuring relative vapor levels of a gas. Steps in the method include: (1) aiming a first infrared emanation sensor toward a wet surface, a first gap being defined between the first sensor and the surface; (2) aiming a second infrared emanation sensor toward a dry surface of a material exhibiting a relatively low heat capacity, a second gap being defined between the second sensor and the dry surface; (3) directing a stream of gas along a path through the first and second gaps; and (4) calculating, based on differences between the infrared sensor readings of the first and second sensors, a vapor level in the gas.

The psychrometer of the present invention can be used to measure the vapor concentration of $H_2O$ and many other substances in a gas. The psychrometer measures relative vapor concentration specifically of the substance which is contained as a liquid in the reservoir chamber. For example, the infrared psychrometer may be used to measure the vapor concentration of ethanol in a gas by filling the reservoir chamber with ethanol so that the wick remains continuously saturated with ethanol. It is also possible to link psychrometers, either in series or in parallel, where one psychrometer has substance X in its reservoir chamber and detects specifically the relative vapor concentration of substance X in a gas, while a second psychrometer has substance Y in its reservoir and detects specifically the relative vapor concentration of substance Y in the same gas.

Also provided by the present invention, is a device for monitoring the temperature of a gas. One such device includes a first infrared emanation sensor, preferably an infrared thermocouple. A first body has a first surface, the first body being relatively dry, non-absorbent and exhibiting a relatively low heat capacity. The first sensor is aimed toward, without contacting the first surface. A second infrared emanation sensor may also be aimed toward, without contacting, a second surface of a second body which is relatively dry, non-absorbent and which exhibits a relatively low heat capacity. The first sensor is positioned opposite the first surface at a first station along a gas channel structure. The second sensor is positioned opposite the second surface at a second station, downstream from the first station, also along the gas channel structure. The difference between the infrared sensor readings at the first station and the second station is indicative of change in temperature of a gas translating through the gas channel structure.

The invention also includes a device for monitoring the evaporative and convective heat loss of a test subject, for example, a newborn. The device includes an enclosure for containing a subject in a controlled environment. The enclosure has an in-port for directing a first stream of gas into the enclosure and an out-port for directing a second stream of gas out of the enclosure. A first psychrometer is operatively linked to the first stream of gas. A second psychrometer is operatively linked to the second stream of gas. At least one of the psychrometers includes an infrared emanation sensor capable of quantitating phase change events occurring at a surface of a moistened absorbent body adjacent the gas stream.

Further contributed by the present invention is a method of measuring temperature in a gas. The steps in this method include: (1) aiming a first infrared emanation sensor toward a dry surface, a gap being defined between the first sensor and the surface; (2) directing a stream of gas along a path extending through that gap; and (3) determining the temperature of gas in the flow through the gap on the basis of sensor readings.

DESCRIPTION OF THE FIGURES

FIG. 3 also illustrates measurement of the absolute temperature of a gas.

DESCRIPTION OF INVENTION

The present invention is useful for measuring the vapor level of a substance in a variety of settings. The invention provides a device and method for monitoring vapor level changes in a gas, instantaneously without the need for a dry gas standard. The invention preferably employs at least one infrared thermocouple which is directed across a gas path, toward, but without contacting, the surface of a moist wick. The wick is saturated with the substance, for example $H_2O$, whose vapor level is to be determined. Changes in the vapor level content of the gas affect the rate of evaporation, and corresponding heat loss at the surface of the wick. Heat loss at the surface of the wick is instantaneously detected by the infrared thermocouple.

Figure 1:
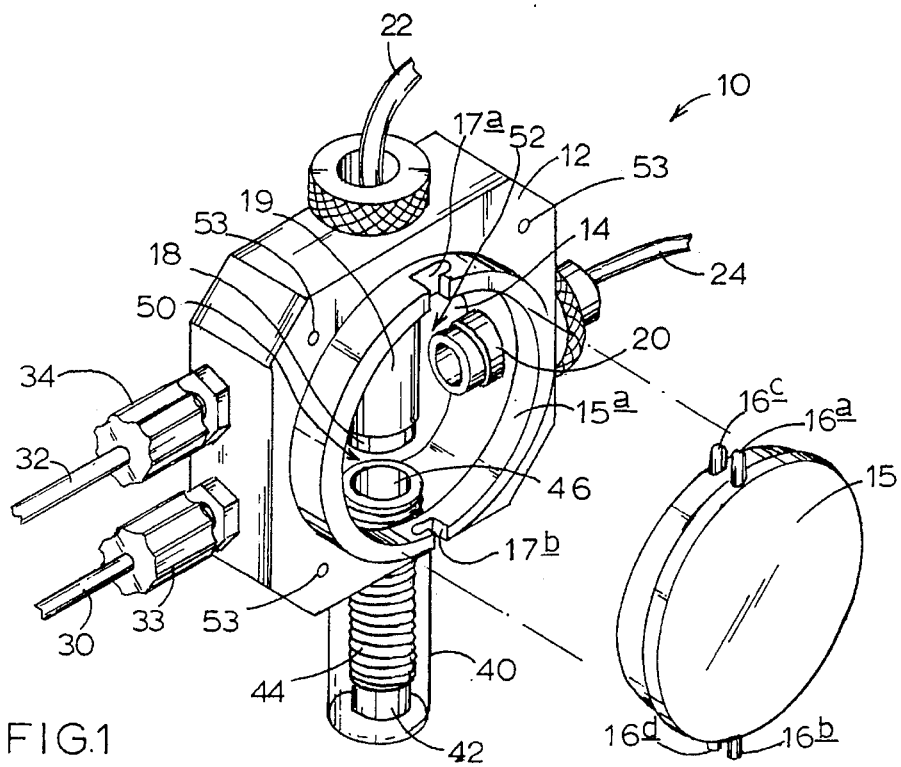
FIG. 1 is a perspective view of a psychrometer employing infrared thermocouples, in accordance with a preferred embodiment of the present invention.
Figure 2:
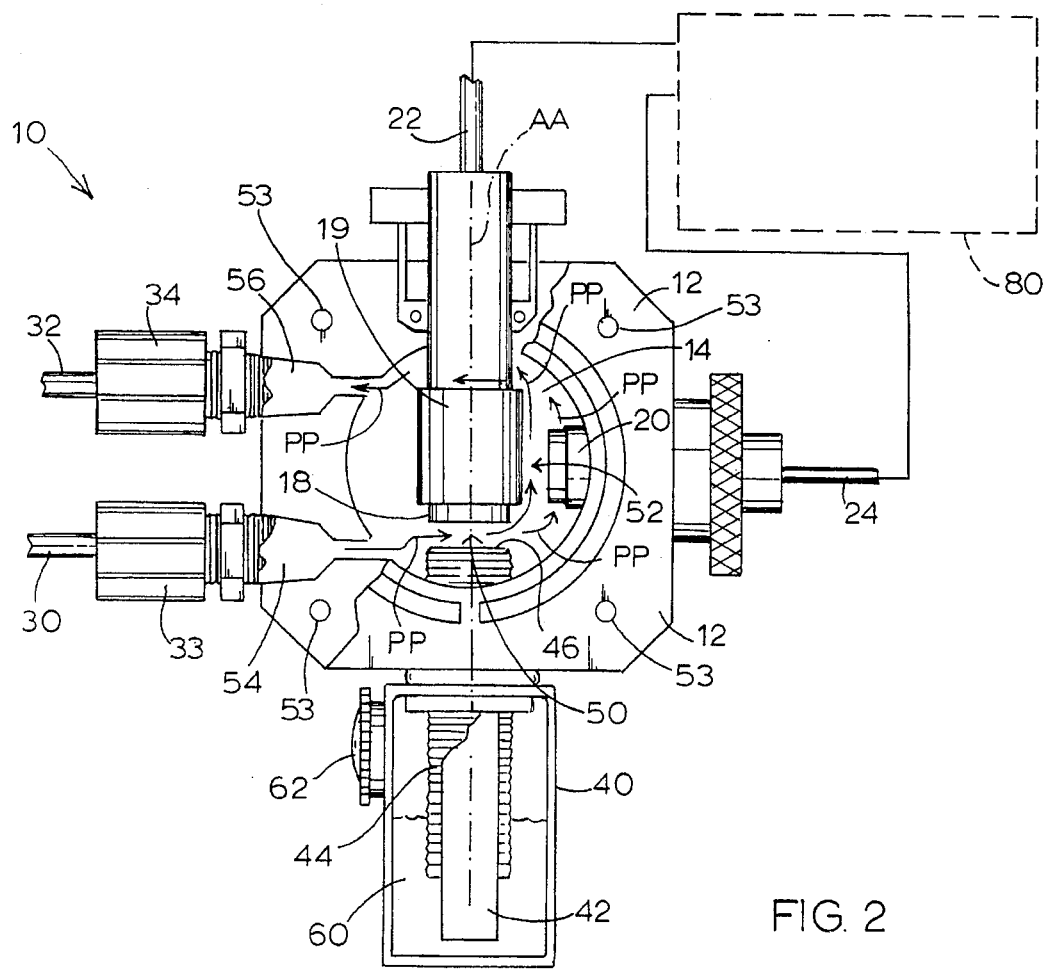
FIG. 2 is a partial cutaway front view of the psychrometer shown in FIG. 1.

FIGS. 1 and 2 illustrate an infrared psychrometer which is used to measure relative water vapor concentrations ("humidity monitoring device"), in accordance with a preferred embodiment of the present invention. FIG. 1 is a perspective view of the psychrometer 10. A housing 12 defines a generally circular chamber 14. Housing 12 is made of an opaque material which is relatively non-absorbent and which exhibits a relatively low heat conductivity. Ideally, housing 12 insulates chamber 14 from the outside environment. For example, the housing can be made out of black Delrin™. A circular door or plug 15 normally covers housing port 15a, and may be removed from housing 12 to provide access to chamber 14. Door 15 has pins 16a and 16b which fit in slots 17a and 17b, respectively. An O-ring is provided around the perimeter of door 15 for sealing chamber 14. Additional pins 16c and 16d are provided on an outer disc portion of door 15 for the purpose of facilitating manipulable rotation of door 15. Within chamber 14, infrared thermocouple 18 is surrounded circumferentially by shroud 19. A second infrared thermocouple 20 also penetrates through housing 12, and is directed or aimed toward shroud 19. The material and thickness of shroud 19 should be selected with the objective in mind that it is desirable for the temperature of the shroud to equilibrate as rapidly as possible with the temperature of the gas flowing adjacent the shroud's surface. The shroud preferably has a wall thickness of about 1/32 of an inch, and the shroud should be made of a material which has a relatively low specific heat or heat capacity, for example, such as the heat capacity exhibited by Delrin™. In a preferred embodiment, thermocouples 18 and 20 are commercially available from Exergen Corporation, under the trademarks IRt/c™ and IRt/c.2™. Each of infrared thermocouples 18 and 20 detects infrared emanation, i.e., temperature, in its field of view, and generates corresponding electrical signals which are transmitted through wires 22 and 24, respectively. The signal levels can be correlated to actual temperature by software with programmable thermocouple input or MV input devices. Gas inlet line 30 and gas outlet line 32 are connected, via fittings 33 and 34, respectively, to the wall of housing 12, and deliver gas in and out of chamber 14.

Translucent (or transparent) chamber 40 contains liquid, for example, $H_2O$ (or whatever substance is being detected in the gas), and is connected to a bottom side of housing 12. A common passage is defined between translucent chamber 40 and chamber 14. An absorbent cotton wick 42 extends from near the bottom of chamber 40, through the passage joining chamber 40 to chamber 14. The diameter of wick 42 is preferably about 3/8 inch. Wick 42 is held in place by a surrounding tube or "wick holder" 44 which is threaded on its external circumferential surface. The threads on the outside of tube 44 facilitate screw-together attachment of chamber 40 to housing 12. Tube 44 also prevents evaporation of liquid from the side of wick 42. A top surface 46 of wick 42 is presented for direct viewing by thermocouple 18. Thermocouple 18 is directed toward wick surface 46 along axis AA which is substantially normal to the wick surface. Surface 46 of wick 42 is constantly supplied with fluid from chamber 40 by capillary action.

Importantly, it can be seen in FIGS. 1 and 2 that neither one of thermocouples 18 or 20 contact the surface which it is aimed at, and of which it is intended to monitor changes in infrared emanation. A gap 50 is defined between thermocouple 18 and wick surface 46. Similarly, a gap 52 is defined between thermocouple 20 and the surface of shroud 19. Infrared thermocouple 18 is not affected by temperature changes inside wick 42, but instead, monitors temperature changes which occur only at the surface 46 of wick 42. No temperature equilibration or delay period is observed. Temperature changes at wick surface 46 are sensed and reported, essentially, within the time it takes for light to travel from surface 46 to thermocouple 18. This feature of the invention, i.e., the ability to monitor exclusively infrared emanation changes at the surface of a wet wick, with speed-of-light quickness, represents a very significant advantage of the present invention over psychrometers in the prior art.

Mounting holes 53 are provided for mounting the psychrometer on a surface, for example, the wall of an incubator. O-rings and/or other junction sealing materials (not shown) may be used to seal chamber 14.

FIG. 2 shows some further details of psychrometer 10. Gas inlet line 30 and gas outlet line 32 access chamber 14 through bores 54 and 56, respectively in the wall of housing 12. Inlet 30 and outlet 32 are preferably ⅜ inch NPT gas in- and outlets A constant supply of evaporative liquid, such as H$_2$O, 60 is maintained in translucent chamber 40. A threaded plug 62 covers an opening in the wall of chamber 40, through which additional liquid can be added. Tile wall of chamber 40 is preferably translucent or transparent so that the user can see how much liquid is in the chamber, and ensure that a minimum level of liquid is maintained. Wick 42 should extend to near the bottom of chamber 40, thus minimizing the amount of liquid which must be in chamber 40 for psychrometer 10 to function properly. As long as some portion of wick 42 is immersed in liquid, upper surface 46 should be wet. Wick 42 should be long enough to block any light from entering chamber 14 through the passage connecting chamber 40 to chamber 14.

Electric signal carrying conduits 22 and 24 convey temperature-indicative signals to a processor 80 such as a computer. A conventional analog-to-digital converter can be used for this purpose, along with software which is designed to process the analog data into readily understandable relative temperature and humidity information.

On a functional level, gas, in which vapor levels are to be monitored, enters chamber 14 through gas inlet line 30. Inside chamber 14 a gas path is at least partially promoted and defined by the geometry of chamber 14 and the structures within it. The basic path of the gas is shown by arrows PP in FIG. 2. A significant portion of the incoming gas first passes through gap 50 between wet wick surface 46 and thermocouple 18. Next, the gas passes through a second gap 52 between an outer surface of shroud 19 and thermocouple 20. The gas then passes around thermocouple 18, and out of chamber 14 through gas outlet line 32. It is desirable to produce gas turbulence in the area of gap 50 for the purpose of avoiding the formation of gas and temperature gradients across gas path PP. Throughout the rest of path PP it is desirable for the gas to flow in a laminar or non-turbulent manner for the purpose of avoiding the generation of heat due to friction. Gas turbulence in gap 50 is created by positioning tube or sleeve 44 in front of gas inlet bore 54. After passing gap 50, the gas flows in a more laminar manner around the other structures in chamber 14.

Basic operative principals of psychrometer 10 can be described with reference to FIG. 2. Each of thermocouples 18 and 20 is set up to detect changes in infrared emanation which occur at a particular surface within chamber 14 along gas path PP. Thermocouple 18 is aimed at a wet surface, in contrast to thermocouple 20 which is aimed at a dry surface. Ideally, shroud 19 is made of material which is black, thin and which exhibits a low heat capacity (such as Delrin™). The goal is for shroud 19 to equilibrate with the temperature of the circulating gas, as rapidly as possible. Both the wet surface and the dry surface which are viewed by thermocouples in chamber 14 are affected by temperature changes of the gas. However, wet wick surface 46 is additionally affected by evaporative heat loss, i.e., temperature drop due to liquid evaporation (change from liquid phase to gas phase). The amount and/or rate of liquid X evaporation at surface 46 is directly affected by the vapor level of substance X in the gas. For example, if the vapor level of substance X decreases in the gas, a corresponding increase in the rate of liquid X evaporation from surface 46 will occur. This will cause the temperature at surface 46 to decrease. In general, the greater the difference between temperature readings from the two thermocouples, the lower the vapor level of substance X in the gas.

Figure 3:
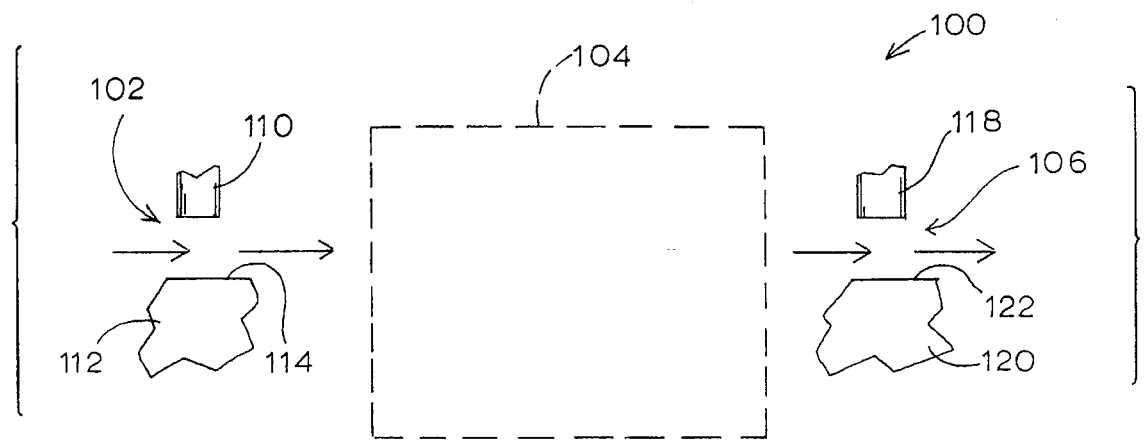
FIG. 3 is a schematic illustration of a device for measuring relative changes in the temperature of a gas.

FIG. 3 illustrates schematically another device ("temperature monitoring device") of the present invention which employs two infrared thermocouples to measure temperature changes in a gas. This device differs principally from the psychrometer previously described, in that both of the thermocouples are aimed at a dry surface. System 100 measures temperature changes of a moving gas between two points along a gas path. System 100 includes a first station 102 which consists of a first body 112 having a first surface 114. A first infrared emanation sensor 110 is aimed toward, without contacting, surface 114. At least a portion of the gas which is to be monitored, passes through a gap defined between infrared emanation sensor 110 and surface 114. The gas then travels through a gas channel structure 104, which may be an incubator or virtually any other type of substantially closed structure. A second station 106 is downstream from station 102, and consists of a second infrared emanation sensor 118 directed toward, without contacting, surface 122 of a second body 120. The gas passes through a gap defined between sensor 118 and surface 122. Bodies 112 and 120 are preferably made of a material which is non-absorbent and which exhibits a relatively low heat capacity. It is desirable for surfaces 114 and 122 to equilibrate rapidly with the temperature of the passing gas.

Figure 4:
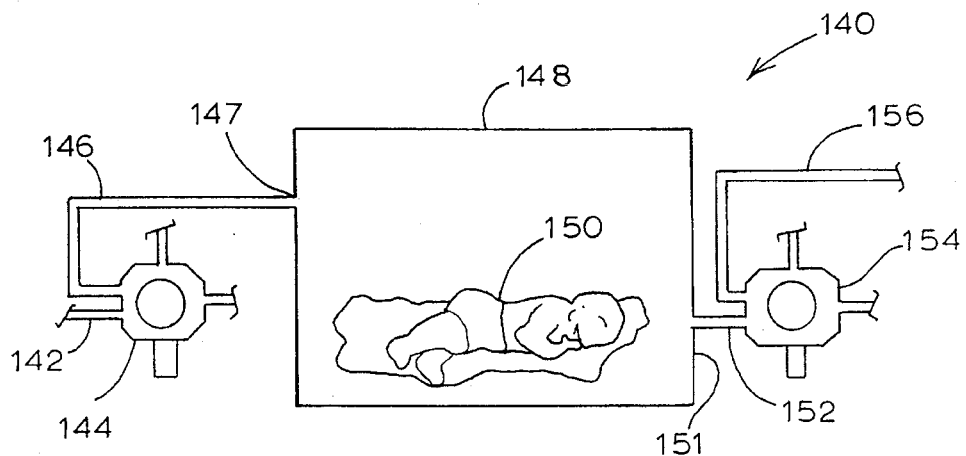
FIG. 4 is a schematic illustration of a device employing two psychrometers for the purpose of monitoring a subject's rates of evaporative and convective heat loss.

A third device of the present invention, as schematically shown in FIG. 4, employs both a humidity measuring device and a temperature measuring device. Device 140, employs two psychrometers, as previously described. The device is used to monitor a test subject's rates of evaporative and convective heat loss. Gas (air) is supplied through gas inlet line 142, into and through psychrometer 144. Gas outlet line 146 carries the gas from psychrometer 144 into a sealed enclosure or incubator 148. Gas outlet line 146 transfers gas through an in-port 147 into sealed enclosure or incubator 148. Incubator 148 contains test subject 150 whose metabolism is being monitored. Gas exits through out-port 151, then through gas inlet line 152 into psychrometer 154. Gas outlet line 156 conveys gas out of psychrometer 154. Each of psychrometers 144 and 154 are essentially the same as the one shown in FIGS. 1 and 2. Device 140 also functions as a temperature measuring device because the difference between dry surface temperature in psychrometers 144 and 154 indicates changes in temperature of the gas as it flows through incubator 148, irrespective of humidity changes. Thus, the infrared thermocouples which are directed toward dry surfaces in psychrometers 144 and 154 are analogous to infrared emanation sensors 110 and 118, respectively, in the temperature monitoring device, schematically illustrated in FIG. 3.

There are essentially three types of observable heat loss from a test subject which are relatable to the subject's rate of metabolism. First, there is radiant heat which is emitted primarily from the subject's skin into the surrounding cavity. Second, there is convective heat transfer from the subject into moving gas around the subject's skin and in the respiratory tract. Third, there is evaporative heat loss which occurs when water, for example, sweat, evaporates from the subject's skin.

Radiant heat loss from the subject is measured with a gradient calorimeter. Convective heat loss from the subject can be measured by comparing the dry surface temperature or infrared emanation reading from psychrometer 144 to the dry surface temperature reading in psychrometer 154 (temperature monitoring device). Evaporative heat loss from subject 150 results in an increase in the level of humidity in the gas. Therefore, evaporative heat loss from the subject can be determined and monitored by comparing the relative humidity reading from psychrometer 144 to the relative humidity reading from psychrometer 154 (humidity monitoring device).

Device 140 can also be used to study or monitor a test subject's internal temperature control system. For this purpose, it is sometimes important to determine the temperature at which a subject begins to sweat. An increase in the amount of liquid water on the subject's skin rapidly translates into an increase in the humidity level of the gas which is detectable by psychrometer 154. Thus, the temperature of the air in incubator 148 can be gradually raised and monitored until psychrometer 154 indicates that the subject is beginning to sweat.

Although preferred embodiments of the invention have been described in detail, the claimed invention, as set forth below, encompasses numerous variations which are apparent in view of the specification and figures. For example, the preferred psychrometer designs of the present invention have been described above in the setting of relative humidity level detection. However, as already explained, the same psychrometer can be used to detect vapor concentrations of virtually any chemical substance which exists in liquid form in the temperature range of normal operation. The psychrometer will detect vapor levels of a specific substance which exists in liquid form in the reservoir and in the wick. The words "wet" and "moist", used throughout the specification to refer to the saturated wick of the psychrometer, should be interpreted to mean absorbed with liquid of any kind, not just water. Thus, many embellishments and modifications of the invention are possible. For instance, a plurality of psychrometers may be set up in series or in parallel, each psychrometer having a different liquid chemical substance in its reservoir, so that vapor levels of different substances in a heterogeneous gas composition can be monitored simultaneously.

I claim:

1. A psychrometer comprising:

a first chamber for containing a liquid X;

a second chamber having a gas inlet, a gas outlet and defining a gas flow path between the inlet and the outlet;

a wick partially immersed in liquid X contained in the first chamber and extending into the second chamber where the wick presents a surface in the gas flow path which receives a constant supply of liquid X by capillary action from the first chamber; and a first infrared thermocouple directed toward, without contacting, the surface of the wick wherein a gap is formed between the thermocouple and the surface of the wick along the gas flow path.

2. The psychrometer of claim 1 further comprising a second infrared thermocouple directed toward a standard, non-absorbent surface present within the second chamber.

3. The psychrometer of claim 2 further comprising a processing device operatively connected to both thermocouples for determining, based on a comparison of signals from the two thermocouples, relative changes in the level of humidity in a gas passing through the second chamber.

4. The psychrometer of claim 1, wherein the second chamber has opaque walls.

5. The psychrometer of claim 4, wherein the first chamber has light-translucent walls.

6. The psychrometer of claim 1 wherein the liquid X is water.

7. The psychrometer of claim 1 wherein the liquid X is nonaqueous.

8. The psychrometer of claim 1, wherein the surface of the wick is substantially contained within a plane and the thermocouple has a viewing direction aimed at the surface of the wick, the viewing direction of the thermocouple being substantially normal to the plane.

9. A psychrometer comprising:

a first chamber having light-translucent walls for containing a liquid X;

a second chamber having opaque walls, a gas inlet and a gas outlet;

a wick partially immersed in liquid X contained in the first chamber and extending into the second chamber where the wick presents a surface which receives a constant supply of liquid X by capillary action from the first chamber;

a first infrared thermocouple directed toward, without contacting, the surface of the wick, wherein the wick is sufficiently opaque to prevent light from the first chamber entering the second chamber.

10. A psychrometer comprising:

a first chamber for containing a liquid X;

a second chamber having a gas inlet, a gas outlet and defining a gas flow path between the inlet and the outlet;

a wick partially immersed in liquid X contained in the first chamber and extending into the second chamber where the wick presents a surface in the gas flow path which receives a constant supply of liquid X by capillary action from the first chamber; and means for monitoring exclusively infrared emanation changes at the surface of the wick.

11. The psychrometer of claim 10 wherein the monitoring of infrared emanation is performed at speed-of-light quickness.

12. A psychrometer comprising:

a gas-flow chamber having a gas inlet, a gas outlet and a gas-flow path between the inlet and the outlet;

a wick including a capillary wetted surface exposed in said chamber; and a dry thermocouple structure exposed in said chamber monitoring psychrometry-selected conditions therein including activity at said wetted surface.

13. A method of measuring changes in the vapor level of a substance in a gas, comprising:

aiming a first infrared emanation sensor toward a wet surface, a first gap being defined between the first sensor and the surface;

aiming a second infrared emanation sensor toward a dry surface of a material, a second gap being defined between the second sensor and the dry surface;

directing a stream of gas along a path through the first and second gaps; and calculating, based on differences between infrared sensor readings of the first and second sensors, a relative vapor level of the substance in the gas.

* * * * *